(12) United States Patent
Scheller et al.

(10) Patent No.: US 8,008,351 B2
(45) Date of Patent: Aug. 30, 2011

(54) METHODS FOR PROPHYLAXIS OR TREATMENT OF CONDITIONS ASSOCIATED WITH CORTICAL SPREADING DEPRESSION

(75) Inventors: Dieter Scheller, Neuss (DE); Thomas Stöhr, Monheim (DE)

(73) Assignee: UCB Pharma GmbH, Monheim (DE)

( * ) Notice: Subject to any disclaimer, the term of this patent is extended or adjusted under 35 U.S.C. 154(b) by 581 days.

(21) Appl. No.: 10/599,976

(22) PCT Filed: Apr. 15, 2005

(86) PCT No.: PCT/EP2005/004047
§ 371 (c)(1),
(2), (4) Date: Aug. 7, 2008

(87) PCT Pub. No.: WO2005/099740
PCT Pub. Date: Oct. 27, 2005

(65) Prior Publication Data
US 2008/0287545 A1    Nov. 20, 2008

Related U.S. Application Data

(60) Provisional application No. 60/562,681, filed on Apr. 16, 2004.

(51) Int. Cl.
*A01N 37/18* (2006.01)
*A61K 31/16* (2006.01)

(52) U.S. Cl. ...................................................... 514/616

(58) Field of Classification Search .................... None
See application file for complete search history.

(56) References Cited

U.S. PATENT DOCUMENTS

| | | | |
|---|---|---|---|
| 4,303,673 A | 12/1981 | Biedermann et al. | 424/324 |
| 4,510,082 A | 4/1985 | Gesellchen et al. | 260/112.5 R |
| 4,513,009 A | 4/1985 | Roques et al. | 514/513 |
| 4,533,657 A | 8/1985 | Morgan | 514/19 |
| 4,618,708 A | 10/1986 | Roques et al. | 562/444 |
| 4,707,468 A | 11/1987 | Yoshino et al. | 514/16 |
| 5,378,729 A | 1/1995 | Kohn et al. | 514/231.2 |
| 5,508,266 A | 4/1996 | Fink | 514/19 |
| 5,536,853 A | 7/1996 | Spellmeyer et al. | 549/441 |
| 5,585,358 A | 12/1996 | Bialer et al. | 514/19 |
| 5,654,301 A | 8/1997 | Kohn et al. | 514/231.2 |
| 5,656,267 A | 8/1997 | Sagen et al. | 424/93.21 |
| 5,760,038 A | 6/1998 | Murugesan et al. | 514/252 |
| 5,773,475 A | 6/1998 | Kohn | 514/616 |
| 5,780,589 A | 7/1998 | Lazarus et al. | 530/331 |
| 5,866,585 A | 2/1999 | Fogel | 514/289 |
| 5,885,999 A | 3/1999 | Elliott et al. | 514/258 |
| 6,001,876 A | 12/1999 | Singh | 514/561 |
| 6,028,102 A | 2/2000 | Bialer et al. | 514/489 |
| 6,037,324 A | 3/2000 | Schwender et al. | 514/18 |
| 6,048,899 A | 4/2000 | Kohn et al. | 514/626 |
| 6,083,941 A | 7/2000 | Farb | 514/177 |
| 6,083,951 A | 7/2000 | Bradbury | 514/256 |
| 6,103,732 A | 8/2000 | Amberg et al. | 514/269 |
| 6,114,390 A | 9/2000 | Engel et al. | 514/595 |
| 6,126,939 A | 10/2000 | Eisenbach-Schwartz et al. | 424/185.1 |
| 6,133,261 A | 10/2000 | Harris | 514/231.2 |
| 6,180,611 B1 | 1/2001 | Montana et al. | 514/19 |
| 6,277,825 B1 | 8/2001 | Olivera et al. | 514/13 |
| 6,737,408 B1 | 5/2004 | Balasubramanium et al. | 514/18 |
| RE38,551 E | 7/2004 | Kohn | 514/616 |
| 6,803,481 B2 | 10/2004 | Selve | 560/157 |
| 6,884,910 B2 | 4/2005 | Harris | 562/553 |
| 7,148,378 B2 | 12/2006 | Harris | 562/553 |
| 7,186,859 B2 | 3/2007 | Harris | 562/553 |
| 7,416,864 B2 | 8/2008 | Stoehr | 435/106 |
| 7,427,601 B2 | 9/2008 | Stoehr | 514/19 |
| 2002/0052418 A1 | 5/2002 | Shirvan et al. | 514/626 |
| 2002/0086828 A1* | 7/2002 | Harris | 514/12 |
| 2003/0216466 A1 | 11/2003 | Scheuerman et al. | 514/513 |
| 2004/0101582 A1 | 5/2004 | Wolicki | 424/760 |
| 2004/0204495 A1 | 10/2004 | Shirvan et al. | 514/616 |
| 2004/0220077 A1 | 11/2004 | Selve | 514/1 |
| 2005/0013856 A1 | 1/2005 | Trivedi et al. | 424/464 |
| 2005/0043675 A1 | 2/2005 | Pastore et al. | 604/67 |
| 2005/0209163 A1 | 9/2005 | Stoehr | 514/19 |
| 2005/0227961 A1 | 10/2005 | Kucharik et al. | 514/211.13 |
| 2005/0261204 A1 | 11/2005 | Stoehr | 514/19 |
| 2005/0277596 A1 | 12/2005 | Stoehr | 514/19 |
| 2005/0288234 A1 | 12/2005 | Stoehr | 514/19 |
| 2006/0009384 A1 | 1/2006 | Rudd et al. | 514/12 |
| 2006/0046957 A1 | 3/2006 | Beyreuther et al. | 514/7 |
| 2006/0100157 A1 | 5/2006 | Rauschkolb-Loffler et al. | 514/18 |
| 2006/0135437 A1 | 6/2006 | Stoehr et al. | 514/19 |
| 2006/0252749 A1 | 11/2006 | Stohr | 514/220 |
| 2007/0042969 A1 | 2/2007 | Rauschkolb-Loffler et al. | 514/19 |
| 2007/0043120 A1 | 2/2007 | Beyreuther et al. | 514/616 |
| 2007/0048372 A1 | 3/2007 | Beyreuther et al. | 424/464 |

(Continued)

FOREIGN PATENT DOCUMENTS

DE    195 33 023    4/1996

(Continued)

OTHER PUBLICATIONS

Abbott et al. (1995) Pain 60:91-102.

(Continued)

*Primary Examiner* — Marcela M Cordero Garcia
(74) *Attorney, Agent, or Firm* — Harness, Dickey & Pierce, P.L.C.

(57) ABSTRACT

The present invention is directed to the use of a class of peptide compounds for the prophylaxis and treatment of chronic headache, particularly migraines.

29 Claims, 1 Drawing Sheet

U.S. PATENT DOCUMENTS

| | | | |
|---|---|---|---|
| 2007/0054962 A1 | 3/2007 | Selve | 514/575 |
| 2007/0197657 A1 | 8/2007 | Beyreuther et al. | 514/616 |
| 2008/0027137 A1 | 1/2008 | Riedner et al. | 514/561 |
| 2008/0280835 A1 | 11/2008 | Beyreuther et al. | 514/2 |
| 2009/0018197 A1 | 1/2009 | Rudd et al. | 514/563 |
| 2009/0018198 A1 | 1/2009 | Stohr | 514/563 |
| 2010/0029543 A1 | 2/2010 | Beyreuther et al. | 514/2 |
| 2010/0099770 A1 | 4/2010 | Selve | 514/616 |
| 2010/0240576 A1 | 9/2010 | Stoehr | 514/17.7 |
| 2010/0256179 A1 | 10/2010 | Stöhr et al. | 514/327 |
| 2010/0256241 A1 | 10/2010 | Stöhr et al. | 562/553 |
| 2010/0260716 A1 | 10/2010 | Stöhr et al. | 424/85.6 |
| 2010/0273714 A1 | 10/2010 | Stoehr | 514/17.7 |
| 2010/0324144 A1 | 12/2010 | Heers et al. | 514/248 |

FOREIGN PATENT DOCUMENTS

| | | |
|---|---|---|
| EP | 0 555 537 | 8/1993 |
| EP | 0 997 147 | 5/2000 |
| EP | 1 243 263 | 11/2002 |
| EP | 1 486 205 | 12/2004 |
| EP | 1 486 206 | 12/2004 |
| EP | 1 537 862 | 6/2005 |
| EP | 1 541 138 | 6/2005 |
| EP | 1 579 858 | 9/2005 |
| EP | 1 688 137 | 8/2006 |
| WO | WO 92/14706 | 9/1992 |
| WO | WO 95/30645 | 11/1995 |
| WO | WO 96/11209 | 4/1996 |
| WO | WO 96/32100 | 10/1996 |
| WO | WO 97/38980 | 10/1997 |
| WO | WO 97/38981 | 10/1997 |
| WO | WO 98/09953 | 3/1998 |
| WO | WO 99/02146 | 1/1999 |
| WO | WO 99/07413 | 2/1999 |
| WO | WO 99/16444 | 4/1999 |
| WO | WO 99/23078 | 5/1999 |
| WO | WO 99/43309 | 9/1999 |
| WO | WO 00/51586 | 9/2000 |
| WO | WO 01/17976 | 3/2001 |
| WO | WO 01/78762 | 10/2001 |
| WO | WO 02/13766 | 2/2002 |
| WO | WO 02/15922 | 2/2002 |
| WO | WO 02/42256 | 5/2002 |
| WO | WO 02/074297 | 9/2002 |
| WO | WO 02/074784 | 9/2002 |
| WO | WO 02/076979 | 10/2002 |
| WO | WO 02/087548 | 11/2002 |
| WO | WO 02/088664 | 11/2002 |
| WO | WO 03/000642 | 1/2003 |
| WO | WO 2004/014895 | 2/2004 |
| WO | WO 2004/043926 | 5/2004 |
| WO | WO 2004/046178 | 6/2004 |
| WO | WO 2004/060353 | 7/2004 |
| WO | WO 2004/066987 | 8/2004 |
| WO | WO 2004/066990 | 8/2004 |
| WO | WO 2004/091585 | 10/2004 |
| WO | WO 2004/100871 | 11/2004 |
| WO | WO 2005/053667 | 6/2005 |
| WO | WO 2005/092313 | 10/2005 |
| WO | WO 2005/099740 | 10/2005 |
| WO | WO 2005/120539 | 12/2005 |

OTHER PUBLICATIONS

Abdulla & Smith (2002) J. Neurophysiol. 88:2518-2529.
Akiba et al. (2003) Receptors & Channels 9:291-299.
Albensi et al. (2004) Am. J. Alzheimer's Disease & Other Dementias 19:269-274.
Amir et al. (2006) J. Pain 7(5 Suppl. 3):S1-S29.
Amér & Meyerson (1988) Pain 33:11-23.
Arnt et al. (1984) Pol. J. Pharmacol. Pharm. 36:221-230.
Arroyo (2003) "Safety of SPM 927 in subjects with epilepsy and neuropathic pain" Poster presented at AES Scientific Exhibit, Dec. 5-10, 2003.
Backonja (2002) Neurology 59:S14-S17.
Backonja (2003) Anesth. Analg. 97:785-790.
Béguin et al. (2003) Bioorganic & Medicinal Chemistry 11:4275-4285.
Béguin et al. (2004) Bioorganic & Medicinal Chemistry 12:3079-3096.
Ben-Menachem (2005) "A dose-response, placebo-controlled trial using lacosamide as adjunctive therapy in subjects with partial seizures" Presented at 26th International Epilepsy Congress, Paris, Aug. 28-Sep. 1, 2005.
Ben-Menachem et al. (2005) "Efficacy and safety of adjunctive oral lacosamide for the treatment of partial-onset seizures in patients with epilepsy" Poster P03.101 presented at American Academy of Neurology 57th Annual Meeting, Miami Beach, FL.
Bennett & Xie (1988) Pain 33(1):87-107 (abstract only http://www.ncbi.nlm.nih.gov/pubmed/2837713).
Bennett et al. (2000) Pain 86:163-175.
Beyak et al. (2004) Am. J. Physiol. Gastrointest. Liver Physiol. 287:G845-G855.
Beyreuther (2004) "Pharmacology of SPM 927 and its relevance to clinical practice for neuropathic pain" Presented at Visiongain Pain Management, 2004.
Beyreuther et al. (2004) "SPM 927 displays potent antinococeptive effects in rat models for inflammatory and neuropathic pain" Poster presented at Neuropathic Pain, May 13-14, 2004.
Beyreuther et al. (2005) "Lacosamide displays antinociceptive effects in a rat model for tumor-induced cancer pain and chemotherapy-induced pain" Poster presented at World Congress on Pain, Aug. 21-26, 2005.
Beyreuther et al. (2005) "Lacosamide displays antinociceptive effects in a rat model for diabetic neuropathic pain" Presented at World Congress on Pain, Aug. 21-26, 2005.
Beyreuther et al. (2006) "Effects of lacosamide as compared to other analgesics: a responder analysis in the streptozotocin rat model for diabetic neuropathic pain" Poster 618 presented at American Pain Society, 2006 (abstract at http://www.ampainsoc.oro/db2/abstract/view?poster_id=2637#618).
Beyreuther et al. (2006) "Lacosamide displays antinociceptive effects in a rat model for musculoskeletal pain induced by TNF" Poster 625 presented at American Pain Society, 2006 (abstract at http://www.ampainsoc.org/db2/abstract/view?poster_id=2643#625).
Beyreuther et al. (2006) "Lacosamide displays antinociceptive effects in rat models for arthritis pain" Poster 626 presented at American Pain Society, 2006 (abstract at http://www.ampainsoc.org/db2/abstract/view?poster_id=2644#626).
Beyreuther et al. (2006) Eur. J. Pharmacol. 539:64-70.
Beyreuther et al. (2007) CNS Drug Rev. 13(1):21-42.
Beyreuther et al. (2007) Arthritis Res. Therapy 9:R14, http://arthritis-research.com/content/9/1/R14.
Bialer et al. (2001) Epilepsy Res. 43:11-58.
Bialer et al. (2002) Epilepsy Res. 51:31-71.
Bilsky et al. (2000) J. Med. Chem. 43:2586-2590.
Biton et al. (2003) Epilepsia 44(Suppl. 9):259, abst. 2.241.
Biton et al. (2004) "Safety and tolerability of lacosamide solution for infusion" Poster presented at AES Scientific Exhibit, Dec. 3-7, 2004.
Biton et al. (2005) "Safety and tolerability of intravenous lacosamide as replacement for oral lacosamide in subjects with partial seizures" Poster P02.148 presented at International Epilepsy Congress, Aug. 28-Sep. 1, 2005.
Biton (2006) "Multicenter, double-blind, double-dummy trial investigating safety, tolerability and pharmacokinetics of intravenous lacosamide (SPM 927) in subjects with partial seizures" Presented at European Congress on Epileptology 2006.
Blackburn-Munro et al. (2002) Eur. J. Pharmacol. 445:231-238.
Blair & Bean (2002) J. Neurosci. 22(23):10277-10290.
Blair & Bean (2003) J. Neurosci. 23(32):10338-10350.
Bolay et al., (2002) "Intrinsic brain activity triggers trigeminal meningeal afferents in a migraine". Nat. Med. 8:136-42.
Bretschneider et al. (2006) http://www.ampainsoc.org/db2/abstract/view?poster_id=2765#766.
Brodie (1996) Can. J. Neurol. Sci. 23(Suppl. 2):S6-S9.
Bunney & Garland (1982) Pharmacopsychiat. 15:111-115.
Caliendo et al. (2005) Curr. Med. Chem. 12(15):1721-1753.
Calvino et al. (1987) Behavioural Brain Res. 24:11-29.

Casey et al. (2003) Neuropsychopharmacol. 28:182-192.
Cawello et al. (2003) Epilepsia 44(Suppl. 9):95, abst. 1.265.
Cawello et al. (2004) Epilepsia 45(Suppl. 7):307, abst. 2.342.
Chen & Lipton (2006) J. Neurochem. 97:1611-1626.
Chevrier et al. (2004) Br. J. Pharmacol. 142:576-584.
Christensen et al. (1996) Pain 68:97-107.
Citrome (2003) Psychopharmacol. Bull. 37(Suppl. 2):74-88.
Colpaert et al. (1982) Life Sciences 31:67-75.
Cummins et al. (2004) J. Neurosci. 24(38):8232-8236.
Daniels et al. (2005) "Long-term safety and efficacy of lacosamide as adjunctive therapy in subjects with partial seizures: 96-week follow-up" Poster presented at AES Scientific Exhibit, Dec. 2-5, 2005.
Decosterd & Woolf (2000) Pain 87:149-158.
Doty et al. (2004) in Bialer et al., Epilepsy Res. 61:1-48, pp. 14-16.
Doty et al. (2004) "Update on the clinical development of SPM 927 (formerly harkoseride)" Presented at EILAT VII, May 2004.
Dowdall et al. (2005) Pharmacol. Biochem. Behavior 80:93-108.
Dubuisson & Dennis (1977) Pain 4:161-174.
Duncan & Kohn (2005) Epilepsy Res. 67:81-87.
Eller et al. (2005) Neurosurg. Focus 18(5):E3, 3 pp.
Elliott (1997) Brain Res. 754:221-226.
Erichsen & Blackburn-Munro (2002) Pain 98:151-161.
Errington et al. (2005) "Lacosamide has a unique molecular mode of action" Poster presented at AES Scientific Exhibit, Dec. 2-5, 2005.
Everill et al. (2001) Neurosci. 106(1):161-169.
Field et al. (1997) Br. J. Pharmacol. 121:1513-1522.
Field et al. (2002) J. Pharmacol. Exp. Ther. 303(2):730-735.
Fountain et al. (2000) Epilepsia 41(Suppl. 7):169.
Freynhagen et al. (2005) Pain 115:254-263.
Grippo et al. (2005) Psychopharmacol. 179:769-780.
Hama et al. (1999) Pharmacol. Biochem. Behavior 62:67-74.
Han et al. (2000) Pain 84:253-261.
Hao et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.
Heers et al. (2006) "The preclinical profile of the novel anticonvulsant lacosamide" Poster presented at European Congress on Epileptology 2006.
Henriksson (1999) Baillière's Clin. Rheumatol. 13(3):455-461.
Hidvegi et al. (2006) "Lacosamide in subjects with painful distal diabetic neuropathy: results of a multi-center, open-label, follow-on trial" Poster presented at American Pain Society, May 3-6, 2006.
Hofmann et al. (2003) Eur. J. Pharmacol. 470:17-25.
Holmberg et al. (2004) J. Med. Chem. 47:3927-3930.
Hong et al. (2004) J. Biol. Chem. 279(28):29341-29350.
Honore et al. (2000) Neurosci. 98(3):585-598.
Horstmann et al. (2002) Epilepsia 43(Suppl. 7):188, abst. 2.174.
Horstmann et al. (2003) Epilepsia 44(Suppl. 9):97, Abst. 1.271.
Horstmann et al. (2003) "SPM 927 does not prolong the QTc interval" Poster presented at 6th International Conference on the Mechanisms and Treatment of Neuropathic Pain, San Francisco, Sep. 18-20, 2003.
Hovinga (2003) IDrugs 6(5):479-485.
Hunskaar et al. (1985) J. Neurosci. Methods 14:69-76.
Hunt (2003) Clin. Orthopaedics Rel. Res. 409:96-105.
Hurley et al. (2002) Anesthesiology 97:1263-1273.
Ilyin et al. (2005) Br. J. Pharmacol. 144:801-812.
Jain (2000) Emerging Drugs 5(2):241-257.
Jensen (2000) Eur. J. Neurol. 7(Suppl. 3):3-4, abst. MT-9.
Kalso (2005) Curr. Pharm. Design 11:3005-3011.
Kemp & McKeman (2002) Nature Neurosci. Suppl. 5:1039-1042.
Kenney et al. (2006) http://www.ampainsoc.org/db2/abstract/view?poster_id=2773#774.
Kim & Chung (1992) Pain 50(3):355-363.
Kropeit et al. (2004) Epilepsia 45(Suppl. 7): 123, abst. 1.323.
Kropeit et al. (2005) "Low drug-interaction potential of Lacosamide" Poster 702 presented at American Pain Society 2005 (abstract at http://www.ampainsoc.org/db2/abstract/view?poster_id=2394#702).
Kropeit et al. (2006) "Lacosamide has low potential for drug-drug-interaction" Poster 851 presented at American Pain Society 2006 (abstract at http://www.ampainsoc.org/db2/abstract/view?poster_id=2848#851).
Lai et al. (2003) Curr. Opin. Neurobiol. 13:291-297.
Lai et al. (2004) Ann. Rev. Pharmacol. Toxicol. 44:371-397.
Lampert et al. (2006) Exp. Brain Res. 174(4):660-666.
Lawand et al. (1997) Eur. J. Pharmacol. 324:169-177.
Leao AAP (1994) "Spreading depression of activity in the cerebral cortex". J. Neurophysiol. 7:359-390.
Lee et al. (2000) NeuroReport 11(4):657-661.
Lee et al. (2002) J. Biol. Chem. 277(8):6542-6549.
Lesser et al. (2004) Neurology 63:2104-2110.
LeTiran et al. (2002) J. Med. Chem. 45:4762-4773.
Lockwood et al. (2002) N. Engl. J. Med. 347(12):904-910.
Lu & Westlund (1999) J. Pharmacol. Exp. Ther. 290:214-219.
Lynch et al. (2004) Pain 110:56-63.
Mach et al. (2002) Neurosci. 113(1):155-166.
Macres (2000) "Understanding neuropathic pain" http://www.spineuniverse.com/displayarticle.php/article1614.html.
Maier et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.
Majumdar et al. (2004) Eur. J. Neurosci. 20:127-143.
March (1985) Advanced Organic Chemistry, New York: Wiley, pp. 16-18.
McCleane (2003) CNS Drugs 17(14):1031-1043.
McCleane et al. (2003) Neurosci. Lett. 352:117-120.
Meinardi (1995) in Levy et al., ed. "Antiepileptic Drugs", 4th ed., chap. 6, pp. 91-97; New York: Raven Press.
Mohapatra et al. (2003) Mol. Cell. Neurosci. 23:314-324.
Moller (2000) J. Am. Acad. Audiol. 11(3):115-124.
Morrow et al. (2001) Soc. Neurosci. Conf. Abst. 508.
Morrow et al. (2003) "The effects of lacosamide in animal models for acute, inflammatory and neuropathic pain" Poster presented at AES Scientific Exhibit, Dec. 5-10, 2003.
Nakata et al. (2003) Biol. Psychiatry 53:571-576.
Papapetropoulos & Singer (2007) Seminars in Neurology 27(2):183-194.
Patel et al. (2001) Pain 90:217-226.
Pessoa-Mahana et al. (2003) Mini Rev. Med. Chem. 3:77-93.
Priestley (2004) Curr. Drug Targets—CNS & Neurol. Disorders 3:441-456.
Randall & Selitto (1957) Arch. Int. Pharmacodyn. 91:409-419.
Rauck et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.
Rauck et al. (2007) Clin. J. Pain 23(2):150-158.
Rauschkolb et al. (2004) "SPM 927, a novel promising pain treatment" Presented at Visiongain Pain Management, 2004.
Remy et al. (2004) Neuropharmacol. 47:1102-1112.
Richeimer (2000) "The Richeimer Pain Update" http:/www.helpforpain.com/arch2000dec.htm.
Rodger (1991) Can. Med. Assoc. J. 145:1571-1581.
Rosenfeld et al. (2003) Epilepsia 44(Suppl. 9):262, abst. 2.249.
Rosenfeld et al. (2005) Epilepsia 46(Suppl. 8):184, abst. 2.278.
Rosenstock et al. (2004) Pain 110:628-638.
Rüttiger et al. (2003) Hear. Res. 180:39-50.
Sachdeo et al. (2003) "An open-label, maximum tolerated dose trial to evaluate oral SPM 927 as adjunctive therapy in patients with partial seizures" Poster presented at 55th Annual Meeting, American Academy of Neurology, Mar. 2003.
Saddi & Abbott (2000) Pain 89:53-63.
Schiltmeyer et al. (2004) Epilepsia 45(Suppl. 7):313, abst. 2.361.
Schiltmeyer et al. (2006) "No interaction between lacosamide and metformin" Poster 850 presented at American Pain Society 2006 (abstract at http://www.ampainsoc.org/db2/abstract/view?poster_id=2847#850).
Seltzer et al. (2001) Pain 93:101-106.

Shaibani et al. (2005) "An open-label follow-on trial to assess the long-term safety and efficacy of oral lacosamide in subjects with diabetic neuropathy" Poster presented at World Congress on Pain, Aug. 21-26, 2005.
Shiro et al. (1996) Psychiatry Clin. Neurosci. 50:141-146.
Silver & Soderlund (2005) Neurotoxicol. 26:397-406.
Sindrup & Jensen (1999) Pain 83:389-400.
Sommerville (2003) "Schwarz Pharma's Neurology Pipeline" http://www.schwarzpharma.com/_uploads/assets/1369_4_neurology_KNS_190203.pdf.
Sommerville & Whitesides (2004) "Intravenous SPM 927 (formerly harkoseride)" Presented at EILAT VII, May 2004.
Stein et al. (1988) Pharmacol. Biochem. Behavior 31:445-451.
Stoehr et al. (2005) "Lacosamide displays potent antinociceptive effects in animal models for neuropathic and inflammatory pain" Poster presented at World Congress on Pain, Aug. 21-26, 2005.
Stoehr & Beyreuther (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.
Stoehr et al. (2006) Eur. J. Pain 10:241-249.
Teng & Abbott (1998) Pain 76:337-347.
Tjølsen (1992) Pain 51:5-17.
Tjølsen & Hole (1997) in Dickinson & Besson, ed., "The Pharmacology of Pain", chap. 1, pp. 1-20; Berlin: Springer-Verlag.
Vaiciene et al. (2006) "Multicenter, open-label trial investigating safety and tolerability of intravenous lacosamide (SPM 927) as replacement for oral lacosamide in subjects with partial seizures: report of first cohort" Poster presented at European Congress on Epileptology 2006.
Vos et al. (1994) J. Neurosci. 14(5):2708-2723.
Watson et al. (1997) Pain 70:53-58.
Wheeler-Aceto et al. (1990) Pain 40:229-238.
Wheeler-Aceto & Cowan (1991) Psychopharmacol. 104:35-44.
Whitesides et al. (2004) "Long-term safety and efficacy of lacosamide as adjunctive therapy in subjects with partial seizures: 48-week follow-up" Poster presented at AES Scientific Exhibit, Dec. 3-7, 2004.
Wood et al. (2002) in "Sodium Channels and Neuronal Hyperexcitability", pp. 159-172; Chichester: Wiley.
Wood et al. (2004) J. Neurobiol. 61:55-71.
Wu et al. (2005) J. Physiol. 565.2:371-380.
Wymer et al. (2005) "A multi-center, randomized double-blind, placebo-controlled trial to assess the efficacy and safety of lacosamide in subjects with painful distal diabetic neuropathy." 8th Int. Conf. on Mechanisms and Treatment of Neuropathic Pain, San Francisco, Nov. 3-5, 2005.
Xu et al. (1992) Pain 48(2):279-290 (abstract only).
Yezierski et al. (1998) Pain 75:141-155.
Ziegler et al. (2005) "Efficacy and safety of lacosamide in the treatment of neuropathic pain attributed to distal diabetic neuropathy." 8th Int. Conf. on Mechanisms and Treatment of Neuropathic Pain, San Francisco, Nov. 3-5, 2005.
Fisher, et al. (2003) "Trigeminal Neuralgia: current treatments and future developments." Expert Opin. Emerging Drugs 8(1):123-143.
Hovinga (2002) "Novel anticonvulsant medications in development." Expert Opin. Investig. Drugs 11(10) 1387-1405.
Ebersberger, et al, (2001) "Is there a correlation between spreading depression, neurogenic inflammation, and Nociception that might cause migraine headach", Ann Neurol 49:7-13.
Iadecola, (2002) "From CSD to headache: a long and winding road", Nature Medicine 8:110-112.
Gorji, (2001) "Spreading depression: a review of the clinical relevance", *Brain Res. Rev.*, 38:33-60.
Office Action dated Mar. 31, 2009 issued in U.S. Appl. No. 11/342,140.
Office Action dated Oct. 21, 2009 issued in U.S. Appl. No. 11/342,140.
Office Action, dated Mar. 5, 2007 issued in U.S. Appl. No. 11/129,376.
Office Action, dated Oct. 16, 2007 issued in U.S. Appl. No. 11/129,376.
Office Action, dated Oct. 20, 2006 issued in U.S. Appl. No. 11/000,951.
Office Action, dated Dec. 11, 2007 issued in U.S. Appl. No. 11/000,951.
Office Action, dated Jan. 22, 2009 issued in U.S. Appl. No. 11/000,951.
Office Action, dated Aug. 19, 2009 issued in U.S. Appl. No. 11/000,951.
Office Action, dated Oct. 2, 2006 issued in U.S. Appl. No. 11/148,429.
Office Action, dated Dec. 7, 2007 issued in U.S. Appl. No. 11/148,429.
Office Action, dated Jul. 28, 2008 issued in U.S. Appl. No. 11/148,429.
Office Action, dated Dec. 17, 2009 issued in U.S. Appl. No. 11/148,429.
Office Action, dated Sep. 11, 2006 issued in U.S. Appl. No. 11/149,181.
Office Action, dated Feb. 5, 2007 issued in U.S. Appl. No. 11/149,181.
Office Action, dated Sep. 27, 2006 issued in U.S. Appl. No. 10/466,295.
Office Action, dated Aug. 8, 2007 issued in U.S. Appl. No. 10/466,295.
Office Action, dated Jun. 4, 2008 issued in U.S. Appl. No. 10/466,295.
Office Action, dated Feb. 19, 2009 issued in U.S. Appl. No. 10/466,295.
Office Action, dated Jul. 22, 2009 issued in U.S. Appl. No. 10/466,295.
Office Action, dated Apr. 17, 2009 issued in U.S. Appl. No. 11/507,110.
Office Action, dated Feb. 3, 2010 issued in U.S. Appl. No. 11/507,110.
Office Action, dated Feb. 1, 2011 issued in U.S. Appl. No. 12/643,665.
Office Action, dated Aug. 19, 2010 issued in U.S. Appl. No. 11/507,110.

* cited by examiner

The Experimental Setting (modified from Paxinos and Watson rat brain atlas)

METHODS FOR PROPHYLAXIS OR TREATMENT OF CONDITIONS ASSOCIATED WITH CORTICAL SPREADING DEPRESSION

This application is a U.S. national stage filing under 35 U.S.C. §371 of International Application No. PCT/EP2005/004047 filed on Apr. 15, 2005, which claims priority of U.S. Provisional Application No. 60/562,681 filed on Apr. 16, 2004. The disclosure of each of the applications identified in this paragraph is incorporated herein by reference in its entirety.

The present invention is directed to the use of a class of peptidic compounds for the prophylaxis and treatment of chronic headache, particularly migraine.

Certain peptides are known to exhibit central nervous system (CNS) activity and are useful in the treatment of epilepsy and other CNS disorders. These peptides which are described in the U.S. Pat. No. 5,378,729 have the Formula (Ia):

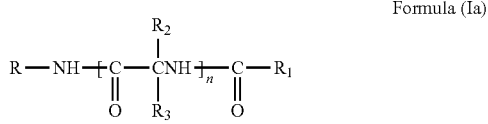

Formula (Ia)

wherein
R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;
$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and
$R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or electron donating group;
Z is O, S, S(O)$_a$, NR$_4$, PR$_4$ or a chemical bond;
Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or
ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_6$ or $PR_4SR_7$, $NR_4PR_5R_6$ or $PR_4NR_5R_7$,

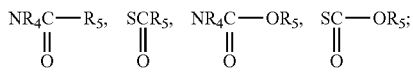

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and
$R_7$ is $R_6$ or $COOR_8$ or $COR_8$;
$R_8$ is hydrogen or lower alkyl, or aryl lower alkyl, and the aryl or alkyl group may be unsubstituted or substituted with an electron withdrawing group or an electron donating group; and n is 14; and
a is 1-3.

U.S. Pat. No. 5,773,475 also discloses additional compounds useful for treating CNS disorders. These compounds are N-benzyl-2-amino-3-methoxy-propionamide having the Formula (IIa):

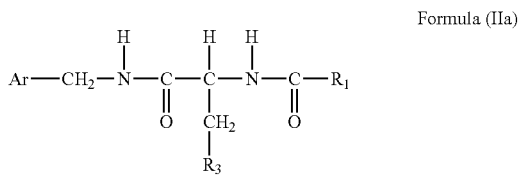

Formula (IIa)

wherein
Ar is aryl which is unsubstituted or substituted with halo; $R_3$ is lower alkoxy; and $R_1$ is methyl.

The U.S. Pat. No. 5,378,729 and U.S. Pat. No. 5,773,475 are hereby incorporated by reference. However, neither of these patents describes the use of these compounds as specific analgesics for the treatment of chronic headache.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) or/and Formula (IIa) showing antinociceptive properties for treating different types and symptoms of acute and chronic pain, especially non neuropathic inflammatory pain, e.g. rheumatoid arthritic pain or/and secondary inflammatory osteo-arthritic pain.

Figure 1:
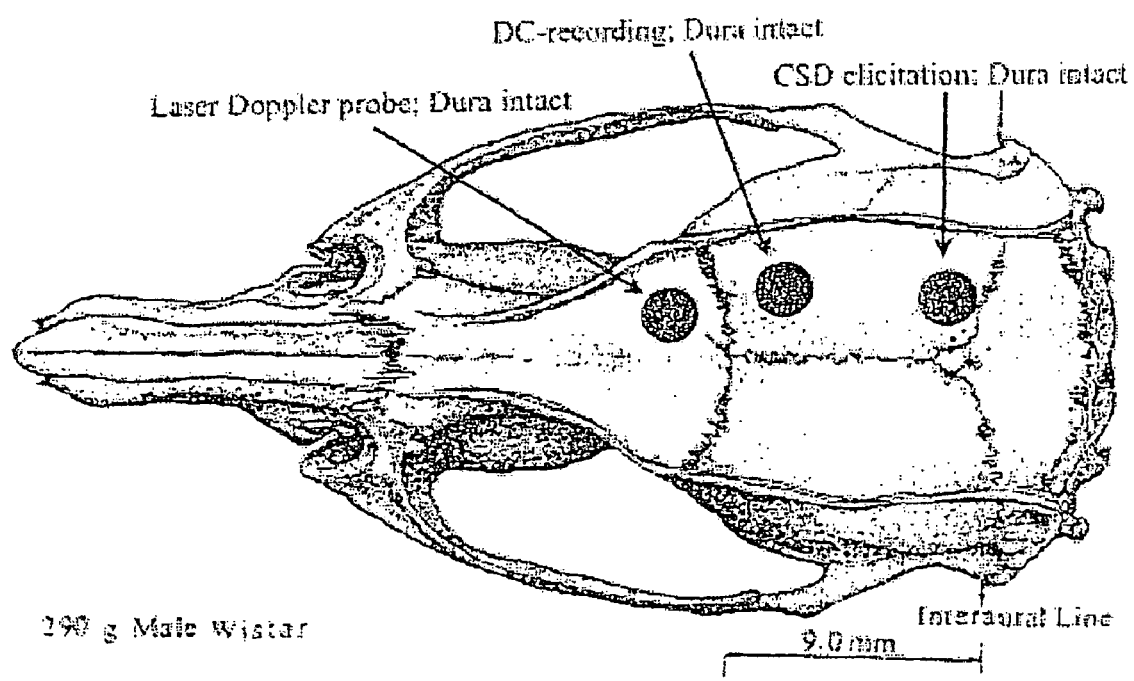
FIG. 1 is a picture demonstrating the location of drill holes in rat brain for the study discussed in the Example herein.

A person suffering from headache can experience pain in several areas of the head, including a network of nerves that extends over the scalp and certain nerves in the face, mouth, and throat. The muscles of the head and the blood vessels found along the surface and at the base of the brain are also sensitive to pain because they contain delicate nerve fibers. The bones of the skull and tissues of the brain itself do not hurt because they lack pain-sensitive nerve fibers. The ends of these pain-sensitive nerves, called nociceptors, can be stimulated by stress, muscular tension, dilated blood vessels, and other headache triggers. Vascular headaches (such as migraines, for instance) are thought to involve abnormal function of the brain's blood vessels or vascular system; muscle contraction headaches appear to involve the tightening or tensing of facial and neck muscles; while traction and inflammatory headaches are symptoms of other disorders, ranging from brain tumor to stroke or sinus infection. Some types of headache are signals of more serious disorders: sudden, severe headache; headache associated with convulsions; headache accompanied by confusion or loss of consciousness; headache following a blow on the head; headache associated with pain in the eye or ear; persistent headache in a person who was previously headache free; recurring headache in children; headache associated with fever; headache that interferes with normal life.

Headaches are diagnosed as vascular, muscle contraction (tension), traction or inflammatory headaches.

The most common type of vascular headache is migraine. Migraine is the most common neurological condition in the developed world. It affects about 10% of the population and is more prevalent than diabetes, epilepsy and asthma combined. Migraine is more than just a headache. It can be a debilitating condition which has a considerable impact on the quality of life of sufferers and their families. Attacks can be completely disabling, forcing the sufferer to abandon everyday activities for up to 3 days. Even in symptom-free periods, sufferers may live in fear of the next attack. The pain of a migraine headache is often described as an intense pulsing or throbbing pain in one area of the head. It is often accompanied by extreme sensitivity to light and sound, nausea, and vomiting. Migraine is three times more common in women than in men. Some individuals can predict the onset of a migraine because it is preceded by an "aura," visual disturbances that appear as flashing lights, zig-zag lines or a temporary loss of vision. People with migraine tend to have recurring attacks triggered by a lack of food or sleep, exposure to light, or hormonal irregularities (only in women). Anxiety, stress or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. There are two ways to approach the treatment of migraine headache with drugs: prevention of the attacks or the relief of the symptoms during the attacks. Many people with migraine use both approaches by taking medications originally developed for epilepsy and depression to prevent future attacks, and treating attacks when they happen with drugs called triptans that relieve pain and restore function.

After migraine, the most common type of vascular headache is the toxic headache produced by fever. Pneumonia, measles, mumps, and tonsillitis are among the diseases that can cause severe toxic vascular headaches. Toxic headaches can also result from the presence of foreign chemicals in the body.

Other kinds of vascular headaches include "clusters," which cause repeated episodes of intense pain, and headaches resulting from a rise in blood pressure. Cluster headaches, named for their repeated occurrence in clusters over weeks or months at roughly the same time of day or night, begin as a minor pain around one eye, eventually spreading to that side of the face. The pain quickly intensifies, compelling the victim to pace the floor or rock in a chair, for instance. Other symptoms include a stuffed and runny nose and a droopy eyelid over a red and weeping eye. Cluster headaches last between 30 and 45 minutes but the relief people feel at the end of an attack is usually mixed with dread as they await a recurrence. Clusters may mysteriously disappear for months or years. Many people have cluster bouts during the spring and fall. At their worst, chronic cluster headaches can last continuously for years. Cluster attacks can strike at any age but usually start between the ages of 20 and 40. Unlike migraine, cluster headaches are more common in men and do not run in families. Paradoxically, both nicotine, which constricts arteries, and alcohol, which dilates them, trigger cluster headaches. The exact connection between these substances and cluster attacks is not known. The sudden start and brief duration of cluster headaches can make them difficult to treat but research scientists have identified several effective drugs for these headaches. The antimigraine drug sumatriptan can subdue a cluster if taken at the first sign of an attack. Injections of dihydroergotamine, a form of ergotamine tartrate, are sometimes used to treat clusters. Corticosteroids also can be used, either orally or by intramuscular injection. For instance, attacks can be prevented by taking anti-epileptic drugs such as valproic acid.

Muscle contraction (tension) type headache is named not only for the role played by stress in triggering the pain, but also for the contraction of neck, face, and scalp muscles brought on by stressful events. Tension headache is a severe but temporary form of muscle-contraction headache. The pain is mild to moderate and feels like pressure is being applied to the head or neck. The headache usually disappears after the period of stress is over. Ninety percent of all headaches are classified as tension/muscle contraction headaches. In contrast, chronic muscle-contraction headaches can last for weeks, months and sometimes years. The pain associated with these headaches is often described as a tight band around the head or a feeling that the head and neck are in a cast. The pain is steady and is usually felt on both sides of the head. Chronic muscle-contraction headaches can cause a sore scalp—even combing one's hair can be painful. In the past, many scientists believed that the primary cause of the pain of muscle-contraction headache was sustained muscle tension. However, a growing number of experts now believe that a far more complex mechanism is responsible.

Occasionally, muscle-contraction headaches will be accompanied by nausea, vomiting, and blurred vision but there is no pre-headache syndrome as with migraine. Muscle-contraction headaches have not been linked to hormones or foods, as has migraine, nor is there a strong hereditary connection. Research has shown that for many people, chronic muscle-contraction headaches are caused by depression and anxiety. These people tend to get their headaches in the early morning or evening when conflicts in the office or home are anticipated. Emotional factors are not the only triggers of muscle-contraction headaches. Certain physical postures that tense head and neck muscles can lead to head and neck pain, such as holding one's chin down while reading, prolonged writing under poor light, holding a phone between the shoulder and ear, or even gum-chewing. Acute tension headaches not associated with a disease are treated with analgesics such as aspirin and acetaminophen. Stronger analgesics, such as propoxyphene and codeine, are sometimes prescribed. Prolonged use of these drugs can lead to dependence, however. People with chronic muscle-contraction headaches may also be helped by taking antidepressants or MAO inhibitors. Mixed muscle-contraction and migraine headaches are sometimes treated with anti-epileptic drugs or barbiturate compounds, which slow down nerve function in the brain and spinal cord.

Like other types of pain, headaches can serve as warning signals for more serious disorders. This is particularly true for headaches caused by traction or inflammation. Traction headaches can occur if the pain-sensitive parts of the head are pulled, stretched, or displaced, as when eye muscles are tensed to compensate for eyestrain, for example. Headaches caused by inflammation include those related to meningitis as well as those resulting from diseases of the sinuses, spine, neck, ears and teeth. Ear and tooth infections as well as glaucoma can cause headaches. In oral and dental disorders, headache is experienced as pain in the entire head, including the face. These headaches are treated by curing the underlying problem. This may involve surgery, antibiotics or other drugs. Characteristics of the various types of more serious traction and inflammatory headaches vary depending on the disorder, these being brain tumors, stroke, spinal taps, trigeminal neuralgia, head trauma, arteritis or meningitis, for example.

Cortical spreading depression (CSD), already described by Leao in 1944 (Leao A A P (1944) *Spreading depression of activity in the cerebral cortex*. J Neurophysiol 7:359-390), is a transient suppression of cortical activity which starts locally and spreads through the tissue with a speed of approximately 3 mm/min. It is associated with the dilatation of pial arterioles, resulting in a cerebral blood flow (CBF) hyperperfusion and followed by a long-lasting hypoperfusion of several hours. The underlying mechanisms and physiological role of these blood flow related changes observed in CSD are still not fully understood. Several vasoactive parenchymal metabolites, such as $K^+$, $CO_2$, adenosine, NO and glutamate, are known to be released during CSD and may contribute to pial vasodilatation. Furthermore, neurotransmitters released from perivascular nerve fibers surrounding cortical pial vessels may also participate in CSD-associated vasodilatation. These neurotransmitters belong mainly to the trigeminal, sympathetic, and parasympathetic nervous systems. Calcitonin gene-related peptide (CGRP), substance P and neurokinin A have been demonstrated immunohistochemically as transmitters of perivascular trigeminal nerves originating in the ipsilateral division of the trigeminal ganglia cells and continue in the nasocillary nerve. The trigeminovascular system is the anatomic substrate for the key hypothesis of migraine pathophysiology. Trigeminal neurotransmitters (like CGRP) contribute substantially to vasodilation in several physiological and pathophysiological conditions. In CSD the brain stem nucleus caudalis becomes activated, as demonstrated by the induction of c-fos, which is blocked by meningeal deafferentation. CSD leads to trigeminal activation and putatively to the release of neurotransmitters from this system.

There is strong evidence that CSD serves as the initiating event for migraine visual aura and pain. Bolay et al. (Bolay H, Reuter U, Dunn A K, Huang Z, Boas D A, Moskowitz M A, 2002, *Intrinsic brain activity triggers trigeminal meningeal afferents in a migraine*, Nat. Med. 8:136-42) established a link between migraine aura and, headache by demonstrating that CSD activates trigeminovascular afferents and evokes a series of cortical meningeal and brainstem events consistent with the development of headache. CSD caused long-lasting blood-flow enhancement selectively within the middle meningeal artery dependent upon trigeminal and parasympathetic activation, and plasma protein leakage within the dura mater in part by a neurokinin-1-receptor mechanism. The findings provide a neural mechanism by which extracerebral cephalic blood flow couples to brain events; this mechanism explains vasodilation during headache and links intense neurometabolic brain activity with the transmission of headache pain by the trigeminal nerve.

A number of evidences suggest involvement of CSD in cerebrovascular diseases. Damage to cerebral tissue during ischemia depends on a complex series of physiological responses and degradative cellular cascades involving a dynamic interplay among the various cells in the region of damaged tissue. Experimental studies support the concept that there is a core of severe ischemia and a focal ischemic insult and that the ischemic core is surrounded by a region of reduced perfusion, the ischemic penumbra. Within the ischemic core, failure of oxygen and glucose delivery leads to rapid depletion of energy stores and cell death. Central to the hypothesis of neuronal salvage is the concept of the ischemic penumbra. The penumbra is an area where metabolic capacity is suppressed but destruction is not yet inevitable. The etiology of progressive cell injury and death in the penumbra zone has been clarified to some extent. Evidence suggests that CSD plays a role in the ischema-infarction tissue damage process. A profound increase in extracellular potassium occurs in the ischemic core. There is a suggestion that the high potassium concentration in the ischemic focus initiates diffusion of potassium ions into the adjacent normally perfused cortex and triggers CSD waves propagating from the rim of the focus to the surrounding intact tissue during the early stages of focal ischemia. These CSD waves cause an additional metabolic burden to the so far intact tissue and thus contribute to the growth of the ischemic core. Generation of CSD has been observed during an approximately 2 h period after ischemia, followed by a shorter interval of increased CSD susceptibility which disappears 3-4 h after the onset of ischemia. Such CSD waves, which are significantly longer than those observed in the intact cortex, can be potentially harmful because they are accompanied by additional release of glutamate and influx of calcium into the neurons. In energy deprived neurons such as seen in the ischemic penumbra this is enough to initiate a cell death cascade. Preventing the occurrence of CSD in the post-ischemic period might therefore reduce ischemic brain damage.

Other clinical indications associated with CSD include intracranial hemorrhage and head injury. Some biochemical changes in the composition of the microenvironment during brain injury, such as high lactate and glucose concentrations in the cerebrospinal fluid, are also observed during CSD. Moreover, in single cases CSD could be observed in the living human cortex of patients with severe head injury. Following intracranial hemorrhage, delayed ischemic deficits are observed. It is believed that CSDs are critically involved in these delayed ischemic deficits (Gorji A. *Spreading depression: a review of the clinical relevance*. Brain Res. Rev. 38, 2001; 33-60). Consequently, a blockade of CSD might prevent the long-term consequences of intracranial hemorrhage and head injury.

Another clinical syndrome associated with CSD is transient global amnesia. Transient global amnesia is characterised by a sudden onset of complete memory loss and learning ability, usually occurring in late middle age. Such amnesic attacks occur, for instance, during migraine aura, during which CSDs have been observed. In animal experiments, the induction of either cortical or subcortical CSD can cause amnesia and learning impairments. This demonstrates that a blockade of CSD might be beneficial for transient global amnesia.

The use of compounds of Formula (Ib) or/and Formula (IIb) for the supression of cortical spreading depression (CSD) has not been reported. Thus, the present invention concerns the use of compounds of Formulae (Ib) or/and (IIb) for the preparation of a pharmaceutical composition for the prevention, alleviation or/and treatment of headache, especially chronic headache such as migraine. Further, the present invention concerns the use of compounds of Formulae (Ib) or/and (IIb) for the preparation of a pharmaceutical composition for the prevention, alleviation or/and treatment of all types of painful conditions associated with or/and caused by CSD, such as, but not limited to, cerebral ischemia during stroke or cardiovascular surgery, for instance, traumatic brain injury, subarachnoid hemorrhage or transient global amnesia. Preferred, but not limited to, is the use of compounds of Formulae (Ib) or/and (IIb) for the preparation of a pharmaceutical composition for the prevention, alleviation or/and treatment of chronic headache associated with or/and caused by CSD such as migraine or other forms of chronic headache of both central and peripheral origin such as, but not limited to, cluster headache, tension-type headache or secondary headaches associated with over use of medication, cranial neuralgias, brain trauma and vascular or metabolic disorders, for example. Especially preferred is the treatment of acute migraine.

Surprisingly, application of compounds (Ib) or/and (IIb), particularly (R)-2-acetamide-N-benzyl-3-methoxypropionamide (SPM 927) exhibited a significant suppression of CSD and a CSD-induced release of calcitonin gene-related peptide (CGRP) in an animal model for migraine.

The invention is applicable in animals, particularly mammals, including humans.

A compound according to the invention useful for the prevention, alleviation or/and treatment of headache or/and conditions associated or/and caused by CSD, particularly chronic headache such as migraine has the general Formula (Ib)

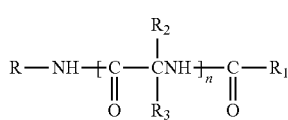

Formula (Ib)

wherein
R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, or/and at least one electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with at least one electron donating group or/and at least one electron withdrawing group;
and $R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or/and at least one electron donating group;

Z is O, S, S(O)$_a$, NR$_4$, NR'$_6$, PR$_4$ or a chemical bond;
Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with at least one electron donating group or/and at least one electron withdrawing group, provided that when Y is halo, Z is a chemical bond, or
ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$, PR$_4$SR$_7$, NR$_4$PR$_5$R$_6$, PR$_4$NR$_5$R$_7$ or N$^+$R$_5$R$_6$R$_7$,

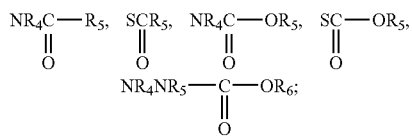

R'$_6$ is hydrogen, lower alkyl, lower alkenyl, or lower alkenyl which may be unsubstituted or substituted with at least one electron withdrawing group or/and at least one electron donating group;

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with at least one electron withdrawing group or/and at least one electron donating group;

$R_7$ is $R_6$ or COOR$_8$ or COR$_8$, which $R_7$ may be unsubstituted or substituted with at least one electron withdrawing group or/and at least one electron donating group;

$R_8$ is hydrogen or lower alkyl, or aryl lower alkyl, and the aryl or alkyl group may be unsubstituted or substituted with at least one electron withdrawing group or/and at least one electron donating group; and n is 14; and
a is 1-3.

Preferably the compound has the general Formula (IIb)

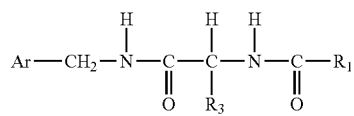

Formula (IIb)

wherein
Ar is aryl, especially phenyl, which is unsubstituted or substituted with at least one halo; $R_3$ is —CH$_2$-Q, wherein Q is lower alkoxy; and $R_1$ is lower alkyl, especially methyl.

The present invention is also directed to a pharmaceutical composition comprising a compound according to Formula (Ib) or/and Formula (IIb) useful for the prevention, alleviation or/and treatment of headache, especially for the prevention, alleviation or/and treatment of headache, or/and a disorder associated with or/and caused by CSD such as migraine.

The compounds of Formula (Ia) are described in U.S. Pat. No. 5,378,729, the contents of which are incorporated by reference.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenethyl, phenylpropyl, phenylisopropyl, phenylbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl. Aryl groups may be unsubstituted or mono or polysubstituted with electron withdrawing or/and electron donating groups as described below.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, halo alkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched. These groups include, for example, formyl, acetyl, propionyl, butyryl, isobutyryl, tertiary butyryl, pentanoyl and hexanoyl.

As employed herein, a heterocyclic group contains at least one sulfur, nitrogen or oxygen ring atom, but also may include several of said atoms in the ring. The heterocyclic groups contemplated by the present invention include heteroaromatics and saturated and partially saturated heterocyclic compounds. These heterocyclics may be monocyclic, bicyclic, tricyclic or polycyclic and are fused rings. They may preferably contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or poly substituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl especially those wherein the phenyl ring thereof is unsubstituted or substituted with electron donating groups or/and electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. Especially preferred electron donating or/and electron withdrawing groups are halo or lower alkoxy, most preferred are fluoro or methoxy. These preferred substituents may be substituted on any one of R, $R_1$, $R_2$, $R_3$, $R_4$, $R_5$, $R_6$, $R'_6$, $R_7$, $R_8$ or/and $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl], and o-hydroxylamino (—O—NH$_2$); alkylamido such as acetamido; trifluoroacetamido; lower alkoxyamino, (e.g., NH(OCH$_3$); and heterocyclicamino, such as pyrazoylamino.

The preferred heterocyclic groups representative of $R_2$ and $R_3$ are monocyclic 5- or 6-membered heterocyclic moieties of the formula:

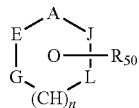

or those corresponding partially or fully saturated form thereof wherein n is 0 or 1; and $R_{50}$ is H or an electron withdrawing group or electron donating group;

A, E, L, J and G are independently CH, or a heteroatom selected from the group consisting of N, O, S;

but when n is, 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is 0, $R_2$ or $R_3$ may additionally be bonded to the main chain by a nitrogen ring atom.

Other preferred moieties of $R_2$ and $R_3$ are hydrogen, aryl, e.g., phenyl, aryl alkyl, e.g., benzyl and alkyl.

It is to be understood that the preferred groups of $R_2$ and $R_3$ may be unsubstituted or mono or poly substituted with electron donating or/and electron withdrawing groups. It is preferred that $R_2$ and $R_3$ are independently hydrogen, lower alkyl, which is either unsubstituted or substituted with electron withdrawing groups or/and electron donating groups, such as lower alkoxy (e.g., methoxy, ethoxy, and the like), N-hydroxylamino, N-lower alkylhydroxyamino, N-loweralkyl-O-loweralkyl and alkylhydroxyamino.

It is preferred that one of $R_2$ and $R_3$ is hydrogen.

It is preferred that n is one.

It is more preferred that n=1 and one of $R_2$ and $R_3$ is hydrogen. It is especially preferred that in this embodiment, $R_2$ is hydrogen and $R_3$ is lower alkyl or ZY;

Z is O, $NR_4$ or $PR_4$; Y is hydrogen or lower alkyl; ZY is $NR_4NR_5R_7$, $NR_4OR_5$, $ONR_4R_7$,

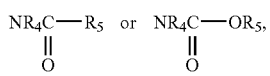

In another especially preferred embodiment, n=1, $R_2$ is hydrogen and $R_3$ is lower alkyl which may be substituted or unsubstituted with an electron donating or electron withdrawing group, $NR_4OR_5$, or $ONR_4R_7$, In yet another especially preferred embodiment, n=1, $R_2$ is hydrogen and $R_3$ is lower alkyl which is unsubstituted or substituted with hydroxy or loweralkoxy, $NR_4OR_5$ or $ONR_4R_7$, wherein $R_4$, $R_5$ and $R_7$ are independently hydrogen or lower alkyl, R is aryl lower alkyl, which aryl group may be unsubstituted or substituted with an electron withdrawing group and $R_1$ is lower alkyl. In this embodiment it is most preferred that aryl is phenyl, which is unsubstituted or substituted with halo.

It is preferred that $R_2$ is hydrogen and $R_3$ is hydrogen, an alkyl group which is unsubstituted or substituted by at least an electron donating or electron withdrawing group or ZY. In this preferred embodiment, it is more preferred that $R_3$ is hydrogen, an alkyl group such as methyl, which is unsubstituted or substituted by an electron donating group, or $NR_4OR_5$ or $ONR_4R_7$, wherein $R_4$, $R_5$ and $R_7$ are independently hydrogen or lower alkyl. It is preferred that the electron donating group is lower alkoxy, and especially methoxy or ethoxy.

It is preferred that $R_2$ and $R_3$ are independently hydrogen, lower alkyl, or ZY;

Z is O, $NR_4$ or $PR_4$;

Y is hydrogen or lower alkyl or

ZY is $NR_4ORR_7$, $NROR_5$, $ONR_4R_7$,

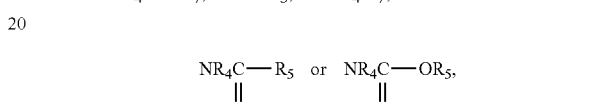

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred $R_1$ is lower alkyl, especially methyl.

It is more preferred that R is aryl lower alkyl and $R_1$ is lower alkyl.

Further preferred compounds are compounds of Formula (Ib) wherein n is 1; $R_2$ is hydrogen; $R_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and $R_1$ is lower alkyl. In this embodiment, it is more preferred that $R_3$ is hydrogen, a lower alkyl group, especially methyl, which may be substituted by electron donating group, such as lower alkoxy, (e.g., methoxy, ethoxy and the like), $NR_4OR_5$ or $ONR_4R_7$ wherein these groups are defined hereinabove.

The most preferred compounds utilized are those of the Formula (IIb):

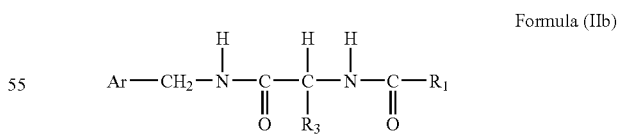

Formula (IIb)

wherein

Ar is aryl, especially phenyl, which is unsubstituted or substituted with at least one electron donating group or electron withdrawing group, especially halo, $R_1$ is lower alkyl, especially containing 1-3 carbon atoms; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, $R_5$ is hydrogen or alkyl containing 1-3 carbon atoms, and $R_7$ is hydrogen or alkyl containing 1-3 carbon atoms.

The most preferred $R_1$ is $CH_3$. The most preferred $R_3$ is $CH_2$-Q, wherein Q is methoxy.

The most preferred aryl is phenyl. The most preferred halo is fluoro.

The most preferred compounds include:
(R)-2-acetamido-N-benzyl-3-methoxy-propionamide,
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

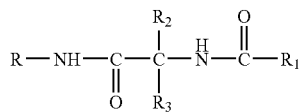

(III)

wherein R, $R_1$, $R_2$, $R_3$, $R_4$, $R_5$, $R_6$, $R'_6$, $R_7$, $R_8$, $R_{50}$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of the utilized compounds is described in U.S. Pat. Nos. 5,378,729 and 5,773,475, the contents of both of which are incorporated by reference.

The compounds utilized in the present invention are useful as such as depicted in the Formulae (Ib) or/and (IIb) or can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of Formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds of the present invention are administered in amounts ranging from about 1 mg to about 100 mg per kilogram of body weight per day. This dosage regimen may be adjusted by the physician to provide the optimum therapeutic response. Patients in need thereof may be treated with doses of the compound of the present invention of at least 100 mg/day, preferably of at least 200 mg/day, more preferably of at least 300 mg/day and most preferably of at least 400 mg/day. At the maximum, a patient in need thereof may be treated with doses at a maximum of 6 g/day, preferably a maximum of 3 g/day, more preferably a maximum of 1 g/day and most preferably a maximum of 400 mg/day.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds of the present invention may be administered which results in a plasma concentration of 7 to 8 μg/ml (trough) and 9 to 12 μg/ml (peak), calculated as an average over a plurality of treated subjects.

A patient in need thereof may be treated with the compounds of the present invention for at least 1 week, preferably at least 2 weeks, more preferably at least 4 weeks, most preferably at least 8 weeks. The dose may be proportionally reduced as indicated by the exigencies of the therapeutic situation.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal, including a human being, in need thereof comprises administering a compound of the present invention in combination with administering a further active agent for the prevention, alleviation or/and treatment of CSD-associated conditions, or/and headache such as migraine. The compound of the present invention and the further active agent for the prevention, alleviation or/and treatment of CSD-associated disorders or/and headache may be administered together, i.e. in a single dose form, or may be administered separately, i.e. in a separate dose form. Thus, the pharmaceutical composition of the present invention may comprise a compound of the present invention as defined above and may additionally comprise a further agent for the prevention, alleviation or/and treatment of CSD-associated disorders or/and headache. The pharmaceutical composition may comprise a single dose form or may comprise a separate dose form comprising a first composition comprising a compound of the present invention as defined above and a second composition for the further agent.

The compounds of the present invention may be used for the preparation of a pharmaceutical composition as described above.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (Iib).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except Insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition or alleviating the patient's disease or condition.

The compounds of the present invention are administered to a patient suffering from the aforementioned type of disorder in an analgesic effective amount. These amounts are equivalent to the therapeutically effective amounts described hereinabove.

The following example shows the properties of SPM927 in reducing pain in a clinical trial in animals with CSD.

The used substance was SPM 927 which is the synonym for Harkoseride. The standard chemical nomenclature is (R)-2-acetamide-N-benzyl-3-methoxypropionamide.

EXAMPLE

This study aims to demonstrate that pre-treatment with SPM 927 (3 doses) affects electrophysiological and biochemical events in a rat model of migraine (Cortical Spreading Depression, CSD). It was shown that SPM 927 treatment reduces the number of CSD-induced direct current (DC)-potentials and Calcitonin gene-related peptide (CGRP) levels in blood.

Materials and Methods

All animal experiments were carried out according to the National Institute of Health (NIH) guidelines for the care and use of laboratory animals, and approved by the Ethical Committee of the National Laboratory Animal Center, Kuopio, Finland. Altogether 77 adult male Wistar rats, purchased from Harlan, Netherlands, and weighing 250-350 g were used for the experiment. Animals were housed at a standard temperature ($22\pm1°$ C.) and in a light-controlled environment (lights on from 7 am to 9 pm) with ad libitum access to food and water. Animals were grouped as follows:

- 15 rats treated with SPM 927 (3 mg/kg; i.p.) 30 min before the CSD episode
- 15 rats treated with SPM 927 (10 mg/kg; i.p.) 30 min before the CSD episode
- 15 rats treated with SPM 927 (30 mg/kg; i.p.) 30 min before the CSD episode
- 15 rats treated with Valproic acid (250 mg/kg; i.p.) 30 min before the CSD episode
- 15 rats treated with Vehicle (2 ml/kg; i.p.) 30 min before CSD episode
- 2 sham rats without CSD episode (topical NaCl application) and without any treatment Subgroups:
- 10 rats to DC-potential, CBF, and blood pH, $pO_2$, $pCO_2$, glucose and mean arterial pressure analysis (rats killed at 30 min after CSD, brains fresh-frozen)
- 5 rats to jugular vein cannulation (CGRP sampling) and dural as well as cortical CGRP immunocytochemistry (rats killed at 15 min after CSD)

Rats were anaethetized with Equithesin (3 ml/kg) and placed in a stereotactic frame. The rectal temperature was maintained at $37.0\pm1.0°$ C. with a homeothermic blanket system. A polyethylene catheter was inserted into the femoral artery in order to monitor arterial blood pressure and take blood samples for arterial pH, $pO_2$, $pCO_2$ and glucose. The arterial blood gases were measured with i-STAT portable clinical analyzer (I-STAT), arterial blood pressure monitored with Cardiocap II blood pressure analyzer (datex-Ohmeda, Helsinki, Finland) and blood glucose with standard glucose meter (Arkray, Japan). The measurements were taken 10 min before as well as 5 min after the CSD episode. The skin was opened by a medical incision and retracted laterally. Three skull burr holes were drilled in a row unilaterally. One was placed over the frontal cortex, the second frontoparietally and the third one parietally (FIG. 1). A laser-Doppler flow probe (Oxyflow, Oxford Optronics, UK) to monitor CBF and a non-invasive tungsten electrode for measuring direct current (DC) potential shifts were placed in the frontal and frontoparietal burr holes on the intact dura, respectively. The laser-Doppler flow probe was positioned in an area free of large pial and dural vessels to minimize a large-vessel contribution to the signal. For the DC-potential measurement, a reference electrode was fixed in the neck. CSDs were elicited unilaterally by placing a KCl-soaked (3.0 M) piece of filter paper on the parietal opening for 5 min. The KCl exposure was terminated by flushing the opening with saline and placing a dry piece of filter paper on the opening. The CBF and DC-potentials were monitored continuously starting from 5 minutes before CSD and continuing up to 30 min after the KCl exposure.

15 min (n=15) after cessation of the 60 min CSD episode, rats were deeply anesthetized with pentobarbital, transcardially perfused first with PBS and then with 4% paraformaldehyde in PBS. After perfusion the supratentorial dura (in toto) and coronal brain blocks were dissected and coronal brain blocks postfixed by immersion in the same fixative for 4 h. The cerebral dura was used as a whole-mount preparation and was subjected to CGRP immunostaining. For the coronal brain specimens, 12 μm thick cryosections on glass slides or 40 μm thick floating sections were cut with a cryostat from the blocks that have been cryoprotected with 20% sucrose for 48 h and frozen in liquid nitrogen-cooled isopentane. Briefly, after PBS washes and blocking serum incubation, the sections were reacted with primary antibody for 48 h at 4° C. (rabbit anti-CGRP, Sigma RBI). The rinsed sections were incubated with biotinylated secondary antibody for 2 h (goat anti-rabbit, Vector Labs, Calif.) then with avidin-biotin complex for 2 h (ABC Elite Kit, Vector Labs), and the peroxidase containing avidin-biotin complex was visualized with 0.05% Ni-diaminobenzidine (Ni-DAB) and 0.02% $H_2O_2$. Finally, the sections were rinsed, air-dried, coverslipped and examined with a Leica 3000RB microscope. The density of immunoreactivity was determined from 3-4 sections in each animal (3-4 different microscopic fields from dura mater).

Following anesthesia (before CSD), a catheter was placed into the right jugular vein. 0.250 ml of blood was taken through the catheter for baseline measurement. For time course experiments further samples were taken at 10-15 and 20-25 min following initiation of CSD. Samples were stored in prepared Eppendorf tubes containing the protease inhibitors aprotinin (1000 KU, Bayer, Germany) and Pefabloc™ (1 mg/ml, Boehringer Mannheim, Germany), immediately cold centrifuged and stored at −80° C. The samples were acidified with trifluoroacetic acid and centrifuged at 6000 g for 20 min. The supernatant was extracted with Sep-Pak C-18 cartridges (Millipore, Waters, UK). Eluates were concentrated (dried) and dissolved in EIA buffer. CGRP concentrations were detected using a commercial CGRP EIA kit (S-3006, Bachem Distribution GmbH) according to the manufacturer's instructions.

All values were calculated as mean±standard deviation (SD) and differences were considered to be statistically significant as the P<0.05 level. Statistical analysis was performed using StatsDirect statistical software. Differences among means were analyzed by using one-way analysis of variance (ANOVA). Dunnet's post-hoc test was applied for multiple comparisons with a control group.

Results

It is shown that SPM 927:
suppresses cortical spreading depression (Table 1)
reduces CSD induced release of CGRP in blood over time (Table 2)

TABLE I

SPM 927 suppresses cortical spreading depression, i.e. reduces the number of direct current (DC) potentials

| Group | Number of DC |
|---|---|
| Saline (n = 10) | 4.5 ± 0.6 |
| SPM 927 (3 mg/kg) (n = 10) | 4.2 ± 0.4 |
| SPM 927 (10 mg/kg) (n = 10) | 3.3 ± 0.4 |
| SPM 927 (30 mg/kg) (n = 10) | 3.5 ± 0.6 |
| Valproic acid (250 mg/kg) (n = 10) | 3.7 ± 0.3 |

TABLE II

SPM 927 reduces cortical spreading depression (CSD) induced CGRP release expressed as percent of baseline levels during the first 25 min after induction of CSD.

| Group | Baseline | 10-15 min | 20-25 min |
|---|---|---|---|
| Saline (n = 5) | 100 ± 0% | 150 ± 30% | 190 ± 24% |
| SPM 927 (3 mg/kg) (n = 5) | 100 ± 0% | 126 ± 45% | 35 ± 7% |
| SPM 927 (10 mg/kg) (n = 5) | 100 ± 0% | 114 ± 27% | 66 ± 31% |
| SPM 927 (30 mg/kg) (n = 5) | 100 ± 0% | 92 ± 53% | 71 ± 12% |
| Valproic acid (250 mg/kg) (n = 5) | 100 ± 0% | 56 ± 8% | 71 ± 15% |

CONCLUSION

These results demonstrate that SPM 927 is useful for the treatment of acute migraine, for the prophylactic treatment of migraine and for the treatment of other forms of chronic headache or/and CSD-associated disorders.

The invention claimed is:

1. A method for treating a condition associated with cortical spreading depression (CSD) in a subject, comprising administering to the subject, in an amount effective to suppress CSD, a compound having the Formula (IIb)

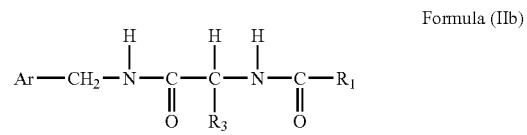

Formula (IIb)

wherein
Ar is phenyl which is unsubstituted or substituted with at least one halo group;
$R_3$ is $CH_2$-Q, wherein Q is lower alkoxy containing 1-3 carbon atoms; and
$R_1$ is lower alkyl containing 1-3 carbon atoms,
or a pharmaceutically acceptable salt thereof, wherein the condition associated with CSD is a chronic headache selected from a group consisting of a muscle contraction headache, a toxic headache, a cluster headache, a traction headache, and an inflammatory headache.

2. The method of claim 1, wherein the compound is (R)-2-acetamido-N-benzyl-3-methoxypropionamide; O-methyl-N-acetyl-D-serine-m-fluorobenzylamide; or O-methyl-N-acetyl-D-serine-p-fluorobenzylamide.

3. The method of claim 1 wherein, in the compound of Formula (IIb), Ar is unsubstituted phenyl.

4. The method of claim 1 wherein, in the compound of Formula (IIb), halo is fluoro.

5. The method of claim 1 wherein, in the compound of Formula (IIb), $R_3$ is $CH_2$-Q, wherein Q is alkoxy containing 1-3 carbon atoms and Ar is unsubstituted phenyl.

6. The method of claim 1, wherein the compound is substantially enantiopure.

7. The method of claim 1, wherein the compound of Formula (IIb) is (R)-2-acetamido-N-benzyl-3-methoxypropionamide.

8. The method of claim 7, wherein the compound is substantially enantiopure.

9. The method of claim 1, wherein the compound is administered at a dose of at least 100 mg/day.

10. The method of claim 1, wherein the compound is administered at a dose of at a maximum 1 g/day.

11. The method of claim 1, wherein the compound is administered at increasing daily doses until a predetermined daily dose is reached which is maintained during further treatment.

12. The method of claim 1, wherein the compound is administered in at most three doses per day.

13. The method of claim 1, wherein administration of the compound results in a plasma concentration of 7 to 8 μg/ml (trough) and 9 to 12 μg/ml (peak).

14. The method of claim 1, wherein the compound is administered for at least one week.

15. The method of claim 1, wherein the compound is administered orally.

16. The method of claim 1, further comprising administering to the subject a further active agent effective for prevention or treatment of a headache or a CSD-associated condition.

17. The method of claim 16, wherein the compound of Formula (IIb) and the further active agent are present in a single dose form.

18. The method of claim 1, wherein the subject is a mammal.

19. The method of claim 18, wherein the subject is human.

20. The method of claim 16, wherein the compound of Formula (IIb) and the further active agent are present in separate dose forms.

21. The method of claim 1, wherein the compound is administered at a dose of at a maximum 1 g/day.

22. The method of claim 1, wherein the compound is administered at a dose of at a maximum 400 mg/day.

23. A method of suppressing CSD to prevent or treat a CSD-initiated headache in a subject in need thereof, the CSD-initiated headache selected from the group consisting of a muscle contraction headache, a toxic headache, a cluster headache, a traction headache, and an inflammatory headache, the method comprising administering to the subject an oral effective amount of (R)-2-acetamido-N-benzyl-3-methoxypropionamide.

24. The method of claim 23, wherein the headache is cluster headache.

25. The method of any one of claims 23 to 24, further comprising administering to the subject a triptan.

26. The method of claim 25, wherein the triptan is sumatriptan.

27. The method of claim 23, comprising orally administering to the subject about 100 mg/day to about 400 mg/day (R)-2-acetamido-N-benzyl-3-methoxypropionamide.

28. The method of claim 16, wherein the further active agent is effective for treatment of a CSD-associated condition selected from the group consisting of head injury, transient global amnesia, and intracranial hemorrhage.

29. A method of treating in a subject a CSD-associated condition selected from the group consisting of a head injury, transient global amnesia, and intracranial hemorrhage, the method comprising administering to the subject an effective amount of (R)-2-acetamido-N-benzyl-3-methoxypropionamide.

* * * * *

UNITED STATES PATENT AND TRADEMARK OFFICE
CERTIFICATE OF CORRECTION

PATENT NO. : 8,008,351 B2
APPLICATION NO. : 10/599976
DATED : August 30, 2011
INVENTOR(S) : Scheller, D. et al.

It is certified that error appears in the above-identified patent and that said Letters Patent is hereby corrected as shown below:

(1) replace "SPR4R6" with -- SPR4R5 -- at column 1, line 51;

(2) replace "n is 14" with -- n is 1-4 -- at column 8, line 13; and (3) replace "NR4ORR7, NROR5, ONR4R7" with -- NR4R5R7, NR4OR5, ONR4R7 -- at column 12, line 18.

Signed and Sealed this
Third Day of January, 2012

David J. Kappos
*Director of the United States Patent and Trademark Office*